(12) United States Patent
Dupont et al.

(10) Patent No.: US 7,635,488 B2
(45) Date of Patent: Dec. 22, 2009

(54) PATCHES AND USES THEREOF

(75) Inventors: Christophe Dupont, Clamart (FR);
Bertrand Dupont, Aix En Provence (FR); Pierre-Yves Vannerom, Paris (FR); Pierre-Henri Benhamou, Paris (FR); Jorge Ronco, Rambouillet (FR)

(73) Assignee: DBV Technologies, Paris (FR)

( * ) Notice: Subject to any disclaimer, the term of this patent is extended or adjusted under 35 U.S.C. 154(b) by 147 days.

(21) Appl. No.: 11/411,531

(22) Filed: Apr. 26, 2006

(65) Prior Publication Data

US 2007/0048361 A1 Mar. 1, 2007

Related U.S. Application Data

(63) Continuation-in-part of application No. 10/659,566, filed on Sep. 10, 2003, which is a continuation of application No. PCT/FR02/00804, filed on Mar. 6, 2002.

(30) Foreign Application Priority Data

Mar. 31, 2001 (FR) .................................. 01 03382

(51) Int. Cl.
*A61L 15/16* (2006.01)
*A61N 1/30* (2006.01)

(52) U.S. Cl. ........................................ 424/448; 604/20
(58) Field of Classification Search ................. 424/448
See application file for complete search history.

(56) References Cited

U.S. PATENT DOCUMENTS

| | | | |
|---|---|---|---|
| 3,212,495 A * | 10/1965 | Osbourn et al. ............. | 600/556 |
| 3,645,852 A | 2/1972 | Axen et al. | |
| 3,837,340 A | 9/1974 | Counter ...................... | 128/260 |
| 3,894,531 A | 7/1975 | Saunders, Jr. .............. | 128/2 W |
| 4,435,180 A | 3/1984 | Leeper | |
| 4,450,844 A | 5/1984 | Quisno ....................... | 128/743 |
| 4,743,249 A * | 5/1988 | Loveland .................... | 424/447 |
| 4,781,705 A | 11/1988 | Shepherd et al. | |
| 4,788,971 A | 12/1988 | Quisno ....................... | 128/743 |
| 4,821,733 A | 4/1989 | Peck | |
| 4,836,217 A | 6/1989 | Fischer ....................... | 128/743 |
| 5,236,455 A | 8/1993 | Wilk et al. | |
| 5,438,984 A | 8/1995 | Schoendorfer | |
| 5,827,608 A | 10/1998 | Rinehart et al. | |
| 6,093,419 A * | 7/2000 | Rolf ............................. | 24/448 |
| 6,142,954 A | 11/2000 | Anhauser et al. | |
| 6,316,598 B1 * | 11/2001 | Van Dyke et al. .......... | 530/357 |
| 2002/0102291 A1 | 8/2002 | Mantelle et al. | |
| 2002/0151487 A1 | 10/2002 | Nickoloff et al. | |
| 2002/0168761 A1 | 11/2002 | Gour et al. | |
| 2003/0064088 A1 | 4/2003 | Carvalho et al. | |
| 2004/0047902 A1 | 3/2004 | Dupont et al. | |
| 2004/0137004 A1 | 7/2004 | Glenn et al. | |
| 2006/0002949 A1 | 1/2006 | Glenn et al. | |
| 2006/0147509 A1 | 7/2006 | Kirkby et al. | |

FOREIGN PATENT DOCUMENTS

| | | |
|---|---|---|
| EP | 0 107 832 A2 | 10/1983 |
| EP | 0409465 A1 | 1/1991 |
| EP | 0976396 A1 | 2/2000 |
| EP | 1031346 A1 | 8/2000 |
| FR | 2527450 A | 12/1983 |
| GB | 501873 A | 3/1939 |
| GB | 1013895 A | 12/1965 |
| JP | 06238008 | 8/1994 |
| JP | 2000-083580 | 12/1999 |
| WO | WO 96/32142 | 10/1996 |
| WO | WO 98/25521 | 6/1998 |
| WO | WO 98/31315 A1 | 7/1998 |
| WO | WO 00/43058 A1 | 7/2000 |
| WO | WO 01/49302 A1 | 7/2001 |
| WO | WO 02/30281 A1 | 4/2002 |
| WO | WO 02/071950 A1 | 9/2002 |
| WO | WO 02/074325 A1 | 9/2002 |
| WO | WO 02/076379 A2 | 10/2002 |
| WO | WO 02/089717 A1 | 11/2002 |
| WO | WO 02/093998 A2 | 11/2002 |
| WO | WO 2004/030696 A2 | 4/2004 |
| WO | WO 2004/052425 A2 | 6/2004 |
| WO | WO 2006/007366 A2 | 1/2006 |

OTHER PUBLICATIONS

Office Action mailed Mar. 22, 2007, U.S. Application No. 10/659,566.
Office Action mailed Jan. 15, 2008, U.S. Application No. 10/659,566.
Office Action mailed Jul. 18, 2008, U.S. Application No. 10/659,566.
Office Action mailed Apr. 17, 2009, U.S. Application No. 10/659,566.
Fentanyl Patch, Brand Name: Duragesic Patches, (2007), pp. 1-6.
Polypropylene, retrieved from http://pslc.ws/mactest/pp.htm, (2005) Polymer Science Learning Center, Department of Polymer Sciences, The University of Southern Mississippi (pp. 1-3).

* cited by examiner

*Primary Examiner*—Sreeni Padmanabhan
*Assistant Examiner*—Timothy E Betton
(74) *Attorney, Agent, or Firm*—Jones Day; Nicola A. Pisano; Jaime D. Choi

(57) ABSTRACT

A patch comprising a support having electrostatic properties is provided wherein a periphery of the support is coated with an adhesive material, and all or part of the non-adhesive surface of the support is covered with at least one biologically active substance in the form of particles that is adhered to the non-adhesive part of the support by electrostatic forces.

42 Claims, 6 Drawing Sheets

Case 1

Case 2

PATCHES AND USES THEREOF

CROSS REFERENCE TO RELATED APPLICATIONS

This application is a continuation-in-part of U.S. application Ser. No. 10/659,566, entitled "Patch for Screening the Sensitization State of a Subject with Respect to an Allergen and Use Thereof" and filed Sep. 10, 2003, which is a continuation of International Application PCT/FR02/00804, filed Mar. 6, 2002 and published, in French, on Sep. 19, 2002 as publication WO 02/071950, and claims priority from French Application No. 01.03382, filed Mar. 31, 2001.

FIELD OF THE INVENTION

The present invention relates, generally, to the delivery or exposure of a substance to a subject using a skin patch and to the uses thereof. The invention also relates to an apparatus for screening for patient sensitivity to an allergen by applying the allergen using a skin patch.

BACKGROUND OF THE INVENTION

Allergy typically is diagnosed using a battery of tests, of which skin tests are most prevalent. An allergy may be diagnosed by testing for skin reactivity on contact with the allergen. A positive result generally presents itself as a local inflammatory skin reaction, which is either moderate in the form of erythema (first clinical element of the inflammatory reaction), or in the form of a papula also indicating the presence of local edema (another component of the inflammatory reaction).

Skin reactivity also may result in response to contact with an allergen other than a contact allergen, such as respiratory or food allergens. That skin reactivity is explained by the constant circulation of immunological elements in the blood, allowing lymphocytes sensitized by the allergens, which have entered the body via the respiratory or digestive tracts, to accumulate within the skin.

Several skin tests are currently known for detecting the sensitization state of an individual with respect to both contact allergens and respiratory and food allergens.

Among these, a test referred to as the "Prick Test" is particularly well-known. The Prick Test may be employed for all allergens capable of triggering an immediate skin reaction to food or respiratory allergens. During this test, a solution containing the allergen is deposited onto the skin, and then the allergen is brought into contact with the immunological elements by means of a stylet or needle, which is used to perforate the superficial part of the dermis that is located adjacent to the solution. The Prick Test is analyzed after half an hour after the allergen is brought into contact with the dermis. In other words, and as already mentioned, this test makes it possible to detect an immediate reaction, which is in general IgE-dependent, i.e. using a type-E immunoglobulin reactivity. The analysis is performed by comparing the reaction at the test site with a positive control site, such as an area exposed to a histamine, and a negative control site, such as an area exposed to physiological saline or the solvent used to dilute the allergens. One drawback of the Prick Test is that it is painful to the patient due to perforation of the dermis with the stylet or needle. Another drawback of the Prick Test is that it is useful only for assessing immediate reactivity. Performing such a test demands the presence of a specialized staff in order to act quickly in case of anaphylactic reaction. This is the reason why the prick test is gradually rejected.

It appears that a number of allergic reactions occur in a delayed or semi-delayed manner, for example within a period of several hours to several days. It has, moreover, been noted that simple contact between the skin and an allergen may cause the appearance of systemic reactions. It is therefore hypothesized that the allergen diffuses through the skin in such a way that it can trigger immediate reactions just as it can trigger delayed reactions.

Accordingly, it has been proposed to deposit an allergen on a support configured to be maintained in contact with the skin for an extended period, so as to allow the allergen to pass through the skin and thus to trigger a skin reaction. Two main types of test have been developed and are known generically as "patch tests".

A first patch test is known under the name FINN CHAMBERS® (a registered trademark of Epitest Ltd. of Tuusula, Finland). It comprises an adhesive support to which are bonded small metal cupules approximately one centimeter in diameter and 2 to 3 millimeters in depth. These cupules receive a diluted allergen mixture deposited onto a cellulose pad supported within the cupule. The mixture is prepared extemporaneously from the native product or from allergens in suspension. The cellulose pad is placed at the bottom of the cupule and the cupule is attached to the patient's skin. The test is analyzed after 48 hours, after removing the material, cleaning the skin and waiting for a short period of time, approximately half an hour, to allow specific local phenomena, associated with the pressure of the edge of the cupule on the skin or with the presence of the adhesive, to disappear.

When using FINN CHAMBERS®, a positive reaction combines erythema, edema and a macular rash at the point of contact, which is compared with any reaction caused by a negative control (cellulose support simply dampened with water). The interpretation is generally easy, but the reaction is not precisely quantifiable. FINN CHAMBERS® may be used to test numerous categories of allergens, whether contact allergens or others. In particular, the allergen/cellulose mixture prepared extemporaneously can, for example, contain foods in order to search for a food allergy, pollen in order to search for a respiratory allergy, or a dye or a metal in order to search for a contact allergy.

While the foregoing method makes it possible to use allergens of infinite variety, it has the drawback of being difficult to use. Specifically, erroneous results may be obtained, for example, due to:

movement of the cellulose pad when the cupule is applied;
contamination of the allergenic mixture, if present in excess amounts, with allergens in neighboring cavities;
use of an allergen concentration that is too low to cause an allergic reaction; and/or
lack of standardization of test results due to variability in the amount of allergen employed from test to test.

Moreover, if the test is used to detect several allergens, there is a risk of confusion during the interpretation, due to the fact that the allergens used cannot be pinpointed on the adhesive supports. In addition, this type of test requires use of allergens that are fresh or in suspension, and which must be solubilized or dispersed in a solvent extemporaneously, i.e. just before the test is applied to the skin.

All of the foregoing factors render results obtained using FINN CHAMBERS® random unless employed by highly trained personnel, thus limiting use of that systems to specialized centers. Consequently, routine use of the foregoing test routinely is limited, especially with respect to doctors' offices.

A patch similar to the FINN CHAMBERS® patch is available under the name LEUKOTEST® (a registered trademark of Cambridge Biotech Corp. of Worcester, Mass.). However, in this device PVC chambers are included in the adhesive support and not bonded to the adhesive support. The chambers contain cellulose pads which are not removable, but remain attached to the cupule. The test is prepared extemporaneously with ready-to-use allergens that are fresh or in suspension. It is easier to use than the FINN CHAMBERS®, but also presents many handling error risks. The following disadvantages are noted:

- the lack of control of the amount of allergen introduced into each chamber;
- the lack of indication concerning the nature of the allergens used on the plastic supports; and also
- the need to have the allergens in a form suitable for deposition on the cellulose pads.

Another type of patch is available under the name T.R.U.E. TEST® (a registered trademark of Mekos Laboratories of Hillerod, Denmark) and is described in U.S. Pat. No. 4,836, 217 to Fischer. The T.R.U.E. TEST® eliminates the presence of the metal cupules, which it substitutes with a gel, into which the allergens are incorporated, the gel being applied directly on an adhesive strip. Only contact allergens can be incorporated into the gel. Thus, if the allergen is soluble in the solvent that is contained in the gel, then the allergen may be directly incorporated into the gel. On the other hand, if the allergen is insoluble, it is necessary to disperse it as homogeneously as possible directly into the gel. The main drawbacks of this type of patch are that is a gel substrate that may interact with the allergen. There can thus be no guarantee that the allergens will be maintained in their organic origin or reactogenic state of origin.

More particularly applied to the case of the allergens, it would be desirable to provide a patch that makes it possible to test all allergens and, in addition, ensures that organic allergens are maintained in their reactogenic state.

It also would be desirable to provide a ready-to-use patch, i.e. a patch which requires no extemporaneous preparation of the allergen prior to application of the patch to a patient or subject.

It further would be desirable to provide a patch capable of containing and delivering, on contact with the skin, a predetermined amount of biologically active substance, which is constant from one patch to another, thereby ensuring that the treatment or test is reliable and reproducible.

SUMMARY OF THE INVENTION

In view of the foregoing, it is an object of the present invention to provide a patch which makes it possible to expose or deliver to or through the skin of a mammalian subject any biologically active substance in the form of a powder.

It is a further object of the present invention to provide a patch that induces perspiration and moistening of the skin in a test area to enhance transcutaneous transport of an active ingredient that is supplied on the patch.

It is another object of this invention to provide a ready-to-use patch, i.e. a patch which requires no extemporaneous preparation of the biologically active substance prior to application of the patch to a patient or subject.

It is a further object of the present invention to provide a patch capable of containing and delivering, on contact with the skin, a predetermined amount of a biologically active substance (e.g., an allergen) which is constant from one patch to another, thereby ensuring that the treatment or test is reliable and reproducible.

It is another object of this invention to provide a patch which makes it possible to test all allergens and, in addition, substantially ensures that organic allergens are maintained in their reactogenic state.

This and other objects of the invention are accomplished by providing a patch comprising an electrostatic support to which a (powdered) biologically active substance is directly or indirectly bound through electrostatic forces, said patch forming a chamber when applied to the skin a subject, allowing a release of the biologically active substance through moistening.

In a particular embodiment, the patch comprises an electrostatic support including a surface having an electrical charge and a powdered biologically active substance, the powdered biologically active substance adhered to a first portion of the electrostatic support by electrostatic forces.

In a preferred embodiment, the patch comprises an adhesive or any other suitable means to immobilize the patch on the skin, typically covering a second portion of the electrostatic support.

In a particular embodiment, the invention resides in a patch comprising a support having electrostatic properties, the periphery of which is coated with an adhesive material, all or part of the non-adhesive surface of the support being directly covered with at least one biologically active substance or ingredient, in the form of particles, the particles being adhered to the non-adhesive surface of the support by electrostatic forces.

A further object of this invention resides in a method of manufacture of a skin patch, comprising:

- providing an electrostatic support having an electrically charged surface;
- providing a powdered active substance; and
- contacting the powdered active substance to the electrostatic support so that the powdered active substance becomes coupled to the electrostatic support by electrostatic forces.

As will be discussed, the biologically active substance or ingredient may be any substance for diagnostic, therapeutic, cosmetic or preventive (for example a vaccine) purposes, such as an allergen, an antigen, a drug, a polypeptide, etc. In a preferred embodiment, the biologically active substance is selected from an allergen, an antigen or a biologically active polypeptide (or peptide). The substance may either be available as a powder or be transformed or treated to become a powder (e.g., through lyophilization, heating and spraying, micronization, etc.).

Regardless of the biologically active substance used, the patch is typically prepared and/or conserved under vacuum. In addition, the patch may have a label, opposite the support, which can be peeled off and which is intended to be removed before the patch is applied to the skin.

A further object of this invention relates to the use of a patch as described above, for screening the sensitization state of a subject with respect to an allergen. The invention also relates to a method for screening the sensitization state of a subject with respect to an allergen, the method comprising applying a patch as described above to the skin, and detecting the presence or absence of a skin reaction.

A further object of this invention also relates to the use of a patch as described above, to induce or stimulate an immune response to an antigen in a subject. More particularly, the invention relates to the use of a patch as described above for epicutaneous vaccination of a subject against an antigen. The invention also relates to a method for inducing or stimulating an immune response to an antigen in a subject, the method comprising applying a patch as described above to the skin of the subject, for a period of time sufficient to allow penetration of the antigen into the skin.

A further object of this invention relates to the use of a patch as described above, to deliver a drug to a subject. More particularly, the invention relates to the use of a patch as described above for transcutaneous drug delivery to a subject. The invention also relates to a method for delivering a drug to a subject, the method comprising applying a patch as described above to the skin for a period of time sufficient to allow delivery of the drug through the skin. The drug may be a synthetic or biological drug, such as a small drug, a protein or a polypeptide (including a peptide). Such drug may be an antibody, a hormone, a cytokine, a growth factor, etc.

The invention allows the use the any biologically active substance in the form of particles in the pure state or after transformation, thus making it possible to involve all substance, whatever their consistency and form in the fresh state. Moreover, the use of allergens in pure, native, whole or fractionated form, i.e. in their reactogenic state of origin, and without any addition of gel, solvent or support, makes it possible not only to have a patch that does not alter the allergen, but also a patch which is ready-to-use, besides the preparation of the skin prior to its application. The invention is also advantageous in that it does not require any treatment of the skin, nor the use of any invasive device (needles, electric current, etc.).

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
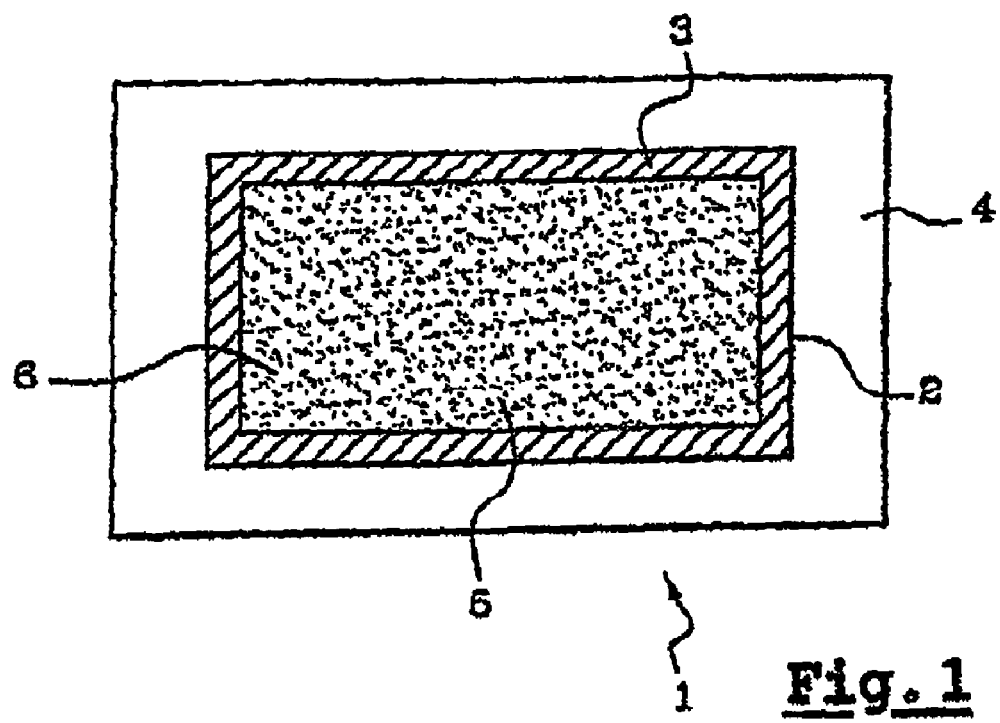
FIG. 1 is a schematic view of an embodiment of a patch according to the present invention.

This invention relates to a patch for delivering or exposing a biologically active substance to or through the epidermis. In particular, the patch may be configured for screening the sensitization state of a subject with respect to an allergen, for epicutaneous vaccination or for drug delivery. Methods of making and using the inventive patch for screening the sensitization state of a subject with respect to an allergen, for vaccination or for drug delivery, are also provided.

DEFINITIONS

As used in this specification, the terms "biologically active substance" and "active ingredient" denote a substance for diagnostic, therapeutic, cosmetic or preventive (for example a vaccine) purposes. The substance may be an allergen, an antigen, a drug, a polypeptide, a nucleic acid, etc. In a preferred embodiment, the biologically active substance is selected from an allergen, an antigen or a biologically active polypeptide (or peptide).

As will be discussed below, the substance is typically "powdered". However, in a particular embodiment, the active substance may alternatively be in a liquid form. In that case, the patch is coated with a neutral powder though electrostatic forces, allowing the support to bind the substance in a liquid form.

The term "powdered", when used in relation to the active substance or ingredient, indicates that the substance is in a solid state, typically in the form of particles, which may be individualized or agglomerated particles. The size of the particles may be adjusted by the skilled person.

The substance may be available naturally or commercially in the form of a powder, i.e. in the form of individualized particles, such that it does not require any particular treatment or transformation, other than perhaps decreasing the size of the particles thereof, if necessary.

The substance may alternatively be available in a more or less large solid form. In this case, it may be first preferred to reduce the substance to individualized particles, optionally after transformation aimed at ensuring its conservation without denaturation.

In a further alternative, the natural substance may be in liquid form. In such a situation, the substance may be lyophilized, so as obtain a powdered form. The powdered form can be obtained by known techniques such as, for example, lyophilization (freezing and sublimation under vacuum) or heating and spraying, the choice of these techniques, in particular the degree of micronization, being left to the assessment of those skilled in the art as a function of the physicochemical characteristics of the substance under consideration.

To ensure conservation of the patch in its packaging, and in particular to avoid modification of the substance by ambient air, the particles typically undergo a particular treatment, such as lyophilization, pasteurization or ionization, and more particularly any treatment known to those skilled in the art.

Within the context of the present invention, the term "electrostatic force" generally designates any non-covalent force involving electric charges. More specifically, this term refers to two kinds of forces, that may act separately or together:

Coulombian forces between space charges of the surface and the ionized particles, Van der Waals forces between the space charges of the surface and the particles, said forces being of three kinds:

permanent dipoles forces, induced dipoles forces, and

London-Van der Waals forces.

The intensity of the force between a surface and a particle can be enhanced or lowered by the presence of a thin water film due to the presence of moisture. Generally, the patch is made and kept in a dry place. The moisture shall be low enough to allow the active ingredient to be conserved. The moisture rate can be regulated in order to get the maximum adhesion forces.

As used herein, the expressions "electrostatic support" and "electret" denote any support made of a material capable of accumulating electrostatic charges, for example, by rubbing, heating or ionization, and of conserving such charges. The electrostatic support typically includes a surface with space charges, which may be dispersed uniformly or not. The charges that appear on one side or the other of the surface of the support may be positive or negative, depending on the material constituting said support, and on the method used to create the charges. In all cases, the positive or negative charges distributed over the surface of the support cause forces of attraction on conducting or non-conducting materials; in the case in point, on the substance in the form of individualized or agglomerated particles. The particles also may be ionized, thereby causing the same type of electrostatic forces of attraction between the particles and the support.

Patch

The invention discloses a novel patch and uses thereof to deliver or expose a substance through or to the skin of a mammalian subject. As discussed above, the substance is directly or indirectly bound to a surface of the patch through electrostatic forces.

In a particular embodiment, the invention relates to a patch comprising an electrostatic support to which a (powdered) biologically active substance is directly or indirectly bound through electrostatic forces, said patch forming a chamber when applied to the skin a subject, allowing a release of the biologically active substance through moistening.

In a further particular embodiment, the invention relates to a skin patch, comprising:
- an electrostatic support;
- a (powdered) biologically active substance bound directly or indirectly to at least a portion of a surface of the support through electrostatic forces; and
- means to maintain the patch on the skin of a mammalian subject, thereby forming a chamber comprising said biologically active substance.

In a particular embodiment, the biologically active substance is powdered, has an electrical charge opposite to the electrical charge of the electrostatic support, or is electrically neutral, and/or is directly adhered to the surface of the support through electrostatic forces.

In a further particular embodiment, the biologically active substance is liquid and is indirectly bound to the surface of the support through a hydrogel which is adhered to the surface of the support through electrostatic forces.

In an other particular embodiment, the means to maintain the patch on the skin comprises an adhesive, that preferably covers a second portion of the electrostatic support.

One of the advantages of the patch of the present invention is that it allows precise metering of the surface mass of the biologically active substance, which is deposited and which is constant from one batch to another, as a function:
- firstly, of the choice of the support and of its ability to store electrical charges on its surface;
- of the type of particles of biologically active substance (e.g., allergen); and
- of the flow of particles during the phase of depositing the biologically active substance (e.g., allergen) on the non-adhesive surface of the support.

In practice, any material can be used as a support provided that it has the required electrostatic qualities. In particular, the support may comprise glass or a polymer chosen from the group comprising cellulose plastics (CA, CP), polyethylene (PE), polyethylen terephtalate (PET), polyvinyl chlorides (PVCs), polypropylenes, polystyrenes, polycarbonates, polyacrylics, in particular poly(methyl methacrylate) (PMMA), fluoropolymers (PTFE for example), etc. The foregoing list is in no way limiting. Glass is particularly advantageous where a hypoallergenic support is desired.

Consequently, the support may be rigid or flexible, may or may not be hydrophilic, and may or may not be translucent, depending on the constituent material. In the case of glass, the support may be made break-resistant by bonding a sheet of plastic to the glass.

In one embodiment, a transparent support is chosen, thus making it possible, where appropriate, to directly observe the appearance of a reaction, without necessarily having to remove the patch.

In order to even further refine the detection of an inflammatory reaction, the patch may have, on the adhesive surface or on the non-adhesive surface, a device sensitive to the physicochemical reactions of the skin noted during the local inflammatory reaction induced e.g., by a positive reaction to an allergen. It may be a colored indicator sensitive to local variations in pH, for example. In this case, it is possible to envisage a reading system facilitating interpretation, independent of the local reaction.

In order to reactivate the electrostatic forces at the surface of the support and thus to reinforce the bonds of the biologically active substance, in particular of the allergen, with the support just before application, the back of the support may be covered with a label which may be peeled off just before application. The label also makes it possible to store the biologically active substance (e.g., allergen) in the dark when the support is at least partially translucent.

Various configurations of the patch may be contemplated. In this respect, in a particular embodiment, the first portion of the electrostatic support to which the substance adheres is a plurality of (substantially parallel, e.g., linear, circular or elliptic) strips and the second portion that comprises a means to maintain the patch on the skin is a plurality of (substantially parallel, e.g., linear, circular or elliptic) strips interposed between adjacent strips of the first portion (see e.g., FIG. 5). The electrostatic support in such a patch may be, e.g., rectangular.

In an other particular embodiment, the first portion of the electrostatic support is circular or elliptic and the second portion circumscribes the first portion. Such a second portion is typically annular, and such an electrostatic support is typically disk-shaped (see e.g., FIG. 3).

In operation, the delivery or exposure to the skin of the biologically active substances (e.g., allergenic molecules) stored in the patch is ensured by the perspiration secreted by the skin within the chamber, i.e., the area delimited, and at least partially occluded, by the patch and which becomes loaded with biologically active substances on contact therewith. The effectiveness of the patch and therefore its sensitivity is therefore greatly conditioned by the creation of a liquid phase, in which the biologically active substance (e.g., allergen) is in solution or in suspension, thus promoting its passage through the pores.

Preferably, the patch makes it possible to (1) prevent evaporation of the perspiration and (2) allow circulation of the perspiration. The first objective is accomplished by making the support water impermeable and using a peripheral adhesive area that forms an airtight joint. In this manner, the patch delimits a hermetically closed space between the skin and the support.

The second objective, i.e., permitting circulation of the perspiration is accomplished by providing a hollow depression formed in the support in the region not coated with adhesive material. This depression is obtained by formatting under hot or under cold conditions, and makes it possible to deposit the biologically active substance (e.g., allergen) in the hollow, such that said biologically active substance is not pressing against the skin and does not alter the blood circulation in the area under consideration. The depression also makes it possible not to bring the biologically active substance (e.g., allergen) into contact with the layer that can be peeled off, which is removed before the patch is applied to the skin. Advantageously, the area defined by the hollow is maintained under vacuum.

It is possible to accelerate or to slow the effect of the patch by altering the configuration of the patch. For example, reducing or increasing the volume of the chamber may be used to alter the amount of time required to release the biologically active substance (e.g., allergen) from the support. In addition, reducing or increasing the permeability of the support may alter the rate at which perspiration occurs which also affects the rate at which the biologically active substance (e.g., allergen) is released. Furthermore, the size of the particles of the biologically active substance may be chosen to provide a desired effect. In particular, for therapeutic patches requiring a quick transport of the active substance, a patch having a chamber as small as possible is desired so that the moisture rate is high enough to trigger a rapid solubilization and transcutaneous transport of the active substance.

In other words, the biologically active substance (e.g., allergen), maintained in an original and reversible manner on the support by electrostatic forces, is entirely released into the cavity when the moisture increases and mixes with the perspiration, which is more readily secreted due to the increase in local heat and to the hypervascularization which ensues therefrom. The penetration of the biologically active substance (e.g., allergen) via the pores of the skin therefore is facilitated and the hypervascularization also allows the influx of immunologically competent elements. The reading, or analysis, of any reaction or treatment may be carried out after the support has been removed and a sufficient amount of time has passed, so as to eliminate any non-specific erythema caused by the adhesive material.

In order to increase the efficacy, the powdered substance is advantageously distributed over the entire surface of the support, in an amount that depends on the biologically active substance (e.g., allergen) employed. As already mentioned, the patch of the present invention advantageously provides a device having a predetermined amount of biologically active substance (e.g., allergen), entirely delivered, which makes it possible to standardize the patches. For example, a patch may comprise substance particles distributed over the support in an amount of between 0.001 and 1 g/cm$^2$.

According to a particular embodiment, the patch exhibits, in the same area, a mixture of several biologically active substances (e.g., allergens).

The invention also relates to a patch kit comprising a plurality of patches as described above, each patch of the kit containing a graduated or constant amount of biologically active substance (e.g., allergen), thus making it possible to increase or maintain the doses over the course of the treatment.

The use of the biologically active substance (e.g., allergen) in the form of particles directly attached to the support, in the dry state, has many advantages. In particular, it makes it possible to avoid any chemical interaction or any reaction which might disturb the function, immunogenicity or allergic process or distort the diagnosis thereof, by bringing only the molecules implicated into contact with the skin. Moreover, the use of the particles makes it possible to conserve the substance in a suitable packaging, such that there is no longer any need to carry out an extemporaneous preparation. Finally, the contact of the particles with the perspiration exuded by the skin makes it possible to obtain a very concentrated solution promoting rapid penetration of the molecules through the epidermis.

As discussed above, the invention may also be used advantageously with active substances in a liquid form. In such a situation, the electrostatic support is typically coated with a neutral powder, such as a hydrophilic polymer, also called hydrogel, allowing the support to bind the substance in a liquid form. Examples of such hydrogels include polyvinylpyrrolidone, polyacrylate of Na, copolymer ether methyl vinyl and maleic anhydride. When putting a liquid on the hydrophilic polymer layer, the polymer particles absorb the liquid and retain it, quickly swelling up and constituting a moistened compound. As soon as the patch is sticked on the skin, the compound is in close contact with the part of the skin located under the backing. In comparison with classical patch-test like Finn Chamber, there are several advantages:

It is very easy to make a patch test, the patch being quite ready to use: the doctor has only to put a drop of liquid onto the backing and the drop is immediately anchored to the patch even if the patch is turned down the release of the substance into the skin is excellent.

The patch may be prepared according to various techniques known per sin in the art. In this respect, in a particular embodiment, the invention relates to a method of manufacture of a skin patch, comprising:

providing an electrostatic support having an electrically charged surface;

providing a powdered active substance, wherein said substance is electrically neutral or has an electrical charge that is opposite to the electrical charge of the electrostatic support;

contacting the powdered active substance to the electrostatic support so that the powdered active substance becomes coupled to the electrostatic support by electrostatic forces.

In a particular embodiment, providing an electrostatic support (electret) comprises:

selecting a film;

heating the film;

applying an electric field to the film for a predetermined duration of time to electrically charge a surface of the film;

cooling the film so the charged surface remains charged; and removing the electric field thereby transforming the film into an electrostatic support having an electrically permanent charged surface.

According to specific embodiments of the method, the film is heated to approximately 80° C., and/or the electric field has a potential of approximately 10 kV; and/or the predetermined duration of time is approximately 15 minutes; and/or the electric field is applied by a corona effect, the corona effect being typically created by a plurality of electrically charged needles spaced apart from the film.

In the above method, the powdered active substance is preferably contacted to the electrostatic support by:

circulating the powdered active substance within a container; and exposing at least a portion of the charged surface of the electrostatic support to the circulating powder.

Alternatively, the powdered active substance may be contacted to the electrostatic support by blowing the powdered active substance toward the charged surface of the electrostatic support with compressed air.

In an another variant, the powdered active substance is contacted to the electrostatic support by attracting the powdered active substance toward the charged surface of the electrostatic support using an electric field.

As discussed above, the powdered active substance may be provided by creating a solid form of an active substance by lyophilization or heating and spraying; and grinding the solid form to create-a solid particles having a predetermined size.

Methods of Testing the Sensitization State of a Subject

The invention also relates to the use of the patch described above, for screening the sensitization state of a subject with respect to an allergen, comprising the step of applying the patch to the skin and then, optionally after removing it, detecting the presence or absence of a skin reaction.

In an advantageous embodiment, the patch is used for screening the sensitization state of a subject with respect to a food allergen contained in the products chosen from the group comprising cow's milk, egg, wheat and peanut.

In another embodiment, the patch is used for screening a subject sensitive to the allergen contained in latex.

The patch of the invention may be used for the diagnosis of contact allergy, by bringing a selected contact allergen into contact with the skin, without the addition of gel, blotter or solvent.

As used herein, the phrase "contact allergen" refers to any allergen capable of causing a reaction on direct contact with the skin, without any reaction at a distance, when said allergen is brought into contact with a subject's body. This type of allergen is found in a certain number of natural or synthetic products which, when they are brought into contact with the skin of a subject, bring about a "contact" allergy which causes a local skin reaction characterized by various phenomena, such as rash, itching, the appearance of vesicles and eczema. Such allergens are entirely known to those skilled in the art and are precisely listed in the literature, such as U.S. Pat. No. 4,836,217. For example, contact allergies are known for metals, such as the nickel contained in watch straps or the chromium contained in cement, allergies to fragrances and to lanolin contained in cosmetic products, allergies to active substances, such as neomycin, flavin contained in certain medicinal products, etc.

The present invention relates not only to contact allergies, but also and especially to all the allergic reactions which may manifest themselves not exclusively by a skin reaction on contact with the allergen, but also by a certain number of symptoms arising at a distance from the site of contact with the allergen, for example anaphylactic shock, diarrhea, sinusitis, asthma, generalized eczema, urticaria, etc. This is true for allergies to acarids, pollens, animal hairs, diverse foods and various substances of plant or animal origin. Many allergens are implicated, thus, for example, acarids, pollens, animal hairs or feathers, etc., which are sometimes referred to as "respiratory" allergens, are the cause of respiratory manifestations of the rhinitis or asthma type. Similarly, groundnut, egg, milk and wheat, which are sometimes referred to as "food" allergens, are the cause of digestive pathologies, such as chronic diarrhea in children, or of anaphylactic pathologies, such as anaphylactic shock, in response, for example, to ingesting groundnut. Allergy to latex is also entirely known and leads to symptoms of the anaphylactic type, causing the patient to run a potentially serious operative risk. The majority of these allergens are described in European Patent 107832.

For use in detecting sensitivity to allergens, it is particularly advantageous to use a transparent support, thus making it possible, where appropriate, to directly observe the appearance of a reaction, without necessarily having to remove the patch.

Also, as discussed above, in order to even further refine the detection of the inflammatory reaction, the patch may have, on the adhesive surface or on the non-adhesive surface, a device sensitive to the physicochemical reactions of the skin noted during the local inflammatory reaction induced by a positive reaction. It may be a colored indicator sensitive to local variations in pH, for example. In this case, it is possible to envisage a reading system facilitating interpretation, independent of the local reaction.

Moreover, and in an advantageous embodiment, the support has an allergen marking device thus enabling the user to avoid registration errors during application or removal of the patch. The marking device may comprise a marking printed on the back of the support that leaves a temporary tattoo on the surface of the skin when the patch is removed, or else of a self-adhesive disk maintained on the adhesive part of the support and which separates therefrom when the patch is removed.

In order to allow triggering of the skin reaction, the particles are distributed over the support in an amount that depends on the allergen employed. As already mentioned, the patch of the present invention advantageously provides a device having a predetermined amount of allergen, entirely delivered, which makes it possible to standardize the patches.

For example, a patch to test for milk allergies may comprise milk particles distributed over the support in an amount of between 0.001 and 1 $g/cm^2$.

In accordance with one aspect of the present invention, the allergen may be employed in the fresh state. In a first embodiment, the natural allergen is in the form of a powder, i.e. already in the form of individualized particles, such that it is not necessarily required to be transformed (for example wheat flour), other than perhaps decreasing the size of the particles thereof.

In another embodiment, the allergen is in a more or less large solid form. In this case, it is first necessary to reduce the allergen to individualized particles, optionally after transformation aimed at ensuring its conservation without denaturation. This is the case, for example, of peanuts in the case of a food allergy to groundnut.

In a third embodiment, the natural allergen is in liquid form. This is the case, for example, of milk, also implicated in some food allergies, which must, in this case, be lyophilized or air dried so as obtain a powdered form. In certain cases, it will be necessary to use only one of the purified fractions of the test allergen. This is the case, for example, of the protein fraction of egg, of albumin, or of cow's milk, or even of the proteins only of lactoserum extracted from cow's milk.

The invention also relates to a patch kit comprising a plurality of patches as described above, each patch of the kit containing a constant or graduated amount of allergen and/or different allergens.

Indeed, the patch of the invention is in particular capable of screening the sensitization state with respect to a given allergen, just as with respect to several allergens at once. In the latter case, the support has several areas having electrostatic properties, advantageously in the form of hollows, each covered with a different test allergen, each electrostatic area being separated by a nonelectrostatic area.

According to another embodiment, the patch exhibits, in the same area, a mixture of several allergens for screening the sensitization state of a subject with respect to a series of given allergens. This may be advantageous, for example, for determining the sensitization state of a subject with respect to a series of food allergens. In the case of the combination of several allergens, either arranged on separate electrostatic supports, or mixed on the same support, the choice of the allergens depends on the lists of allergens implicated in the most common pathologies in agreement with the data from the literature. This choice is made so as to form combinations specific for each pathological context in each one of the major age brackets. These lists of allergens are, moreover, able to be modified as a function of the food habits and of the environmental conditions specific to the places where the patches are distributed. In certain cases, the allergens can be chosen from any list published by the health authorities.

An object of this invention therefore relates to a method for screening the sensitization state of a subject with respect to an allergen, the method comprising applying a patch as described above to the skin, and detecting the presence or absence of a skin reaction.

An object of this invention also relates to a method for detecting the response of a subject with respect to an allergen, the method comprising applying a patch as described above to the skin, and detecting the presence or absence of a skin reaction.

In a particular embodiment E-patch technology is also used for testing the state of sensitization with respect to an allergen in a liquid form. In fact, a lot of allergen extracts are in solution and are sold to the doctors in such a form. In order to allow the use of such extracts with an electrostatic patch of this invention, the electrostatic support of the patch is not directly coated with the active ingredient but with a neutral powder which is preferably a hydrophilic polymer, also called hydrogel. The coating process of such a polymer is very similar with that of an active ingredient; grinding and carrying the particles on the electret in order to form a regular and thin powder layer on it. When putting a liquid on the hydrophilic polymer layer, the polymer particles absorb the liquid and retain it, quickly swelling up and constituting a moistered compound. As soon as the patch is sticked on the skin, the compound is in close contact with the part of the skin located under the backing.

Methods of Vaccination or Desensitization

In addition to its use for detecting sensitivity to an allergen, the patch of the invention may also be used for desensitizing a subject to one or more given antigens, or for vaccination purposes. In this case, the patch is applied to the skin for a given amount of time depending on the amount of allergen to be delivered. Patches containing increasing or constant amounts of antigens may be used. A programmed release of the antigen from the patch thus advantageously may be envisioned.

A further object of this invention therefore also relates to the use of a patch as described above, to induce or stimulate or modulate an immune response to an antigen in a subject, particularly an antibody response, cellular immunity or regulatory cells. The immune response elicited could be with the aim of protecting individuals against a pathogen or an illness such as cancer or autoimmunity. The immune response elicited could be with the aim of treating individuals against chronic infections or an illness such as cancer or autoimmunity.

A further object of this invention relates to the use of a patch as described above for epicutaneous vaccination of a subject against an antigen.

A further object of this invention relates to the use of a patch as described above for epicutaneous vaccination of a subject against an antigen formulated with an adjuvant.

A further object of this invention relates to the use of a patch as described above for epicutaneous administration of an immuno-stimulatory (adjuvant) compound close to the site of subcutaneous or intramuscular vaccine injection of a subject against an antigen.

The invention also relates to a method for inducing or stimulating an immune response to an antigen in a subject, the method comprising applying a patch as described above to the skin of the subject for a period of time sufficient to deliver an effective amount of said antigen.

The invention also relates to a method of desensitizing a subject to one or more allergens, the method comprising applying a patch as described above to the skin of the subject for a period of time sufficient to deliver desensitizing amounts of the allergen.

The invention also relates to a patch kit comprising a plurality of patches as described above, each patch of the kit containing a graduated or a constant amount of allergen thus making it possible to increase the allergen doses over the course of the desensitization treatment.

Transcutaneous immunization (TCI), topical application of vaccine formulation on the skin, provides access to the skin immune system which is dominated by densely distributed and potent antigen presenting cells (Langerhans cells (LC)), that can be stimulated to orchestrate specific and robust immune responses (Babiuk, Baca-Estrada et al. 2000, "Cutaneous vaccination: the skin as an immunologically active tissue and the challenge of antigen delivery." *J Control Release* 66(2-3): 199-214.). In recent years, the potential for exploitation of the skin for purposes of vaccination has received a great deal of attention. Initial skepticism regarding TCI and the revelation that large molecules in simple solution could in fact penetrate the skin has led different laboratories to address further questions, including the induction of robust immune responses, adjuvant use, induction of functional systemic immune responses, size restriction of antigens, etc. (Glenn, Scharton-Kersten et al. 1999, "Advances in vaccine delivery: transcutaneous immunisation." *Expert Opin Investig Drugs* 8(6): 797-805; Kaiserlian and Etchart 1999 "Epicutaneous and transcutaneous immunization using DNA or proteins." *Eur J Dermatol* 9(3): 169-76; Partidos, Beignon et al. 2003, "Delivering vaccines into the skin without needles and syringes." *Expert Rev Vaccines* 2(6): 753-61; "Immunity under the skin: potential application for topical delivery of vaccines." *Vaccine* 21(7-8): 776-80.)

The exploitation of normal immune defense mechanisms for the purposes of immunoprotection or immunomodulation can be achieved by the application of a skin patch of this invention. In particular, the invention shows that a patch of this invention can be used for TCI, thereby inducing systemic antibody immune responses in a subject, and that these responses can be exploited for immunization strategies.

For TCI, any antigen may be used or delivered with the present invention, such as peptides, proteins, nucleic acids, etc. Typically, the antigen is a protein, or a polypeptide or a peptide comprising at least one epitope. The antigen may be any naturally-occurring antigen, which may be produced by techniques known in the art, such as synthetic or recombinant technologies. In a particular embodiment, the antigen comprises a peptide or a mixture of distinct peptides. Also, specific formulations comprising adjuvants and/or skin hydration enhancer may be used for such an indication. The invention may be used to induce an immune response against various types of agents, such as viruses, bacteria, fungus, parasites, toxins, auto-antigens, tumors, etc.

Methods of Drug Delivery

The patch of the invention may also be used to administer a biologically active substance to a subject, e.g., for the purpose of obtaining a therapeutic (medicinal product), dietetic, diagnostic (e.g., contrast agent) or cosmetic action.

The invention indeed shows that molecules exposed to the skin surface using a patch of this invention are able to penetrate the skin and diffuse within the body. Accordingly, the patch of this invention can also be used to deliver active molecules through transcutaneous delivery.

The invention may be used to deliver any type of active molecule, such as small drugs, proteins, polypeptides peptides, nucleic acids, etc. In a particular embodiment, the invention is used to deliver polypeptides (or peptides) having biological activity, such as hormones, growth factors, cytokines, enzymes, clotting factors, etc.

An object of this invention thus resides in a method of delivering a biologically active molecule to a subject, the method comprising applying to the skin of a subject a patch as described above containing said molecule, for a period of time sufficient to allow delivery. The patch as used in this embodiment preferably has a limited chamber, to increase the efficacy of the delivery.

A further object of this invention also relates to the use of a patch as described above, to deliver a drug to a subject. More particularly, the invention relates to the use of a patch as described above for transcutaneous drug delivery to a subject. The invention also relates to a method for delivering a drug to a subject, the method comprising applying a patch as described above to the skin.

Referring to FIG. 1, an illustrative embodiment of a patch constructed in accordance with the principles of the present invention is described. Patch 1 comprises electrostatic support 2 made, for example, of polyethylene the periphery of which is coated with adhesive material 3. The back of support 2 is covered with label 4, which may be peeled off. Allergen 5 is distributed in pulverulent, or powdered, form over non-adhesive area 6 of support 2.

Figure 2:
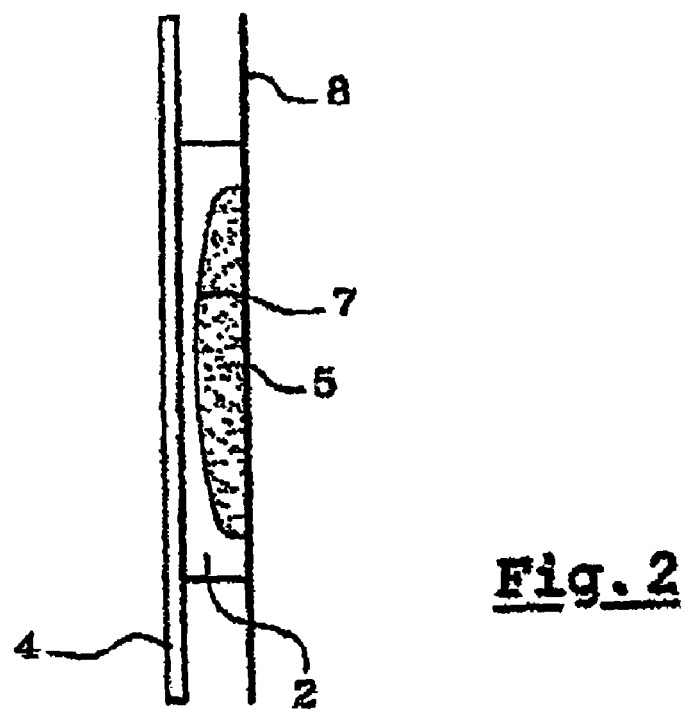
FIG. 2 is a cross-sectional view of the patch of FIG. 1.

With respect to FIG. 2, support 2 has depression 7 disposed over the non-adhesive surface to which individualized particles of allergen 5 are adhered. Patch 1 includes second label 8, which can be peeled off, that faces support 2 and label 4. Label 8 is removed before the patch is applied to the area under consideration.

Figure 3:
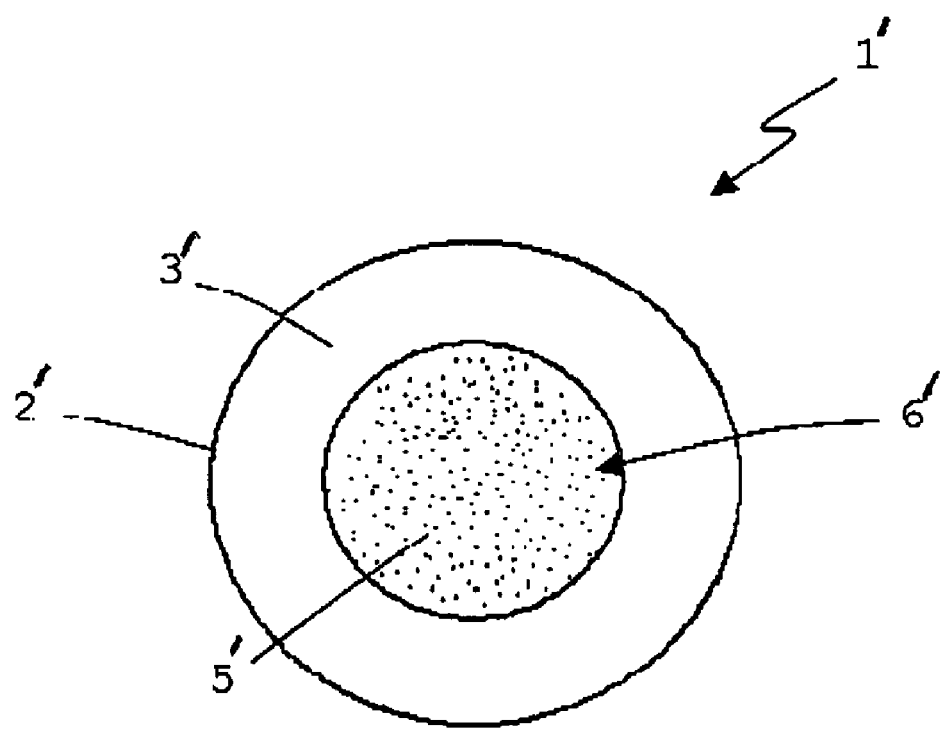
FIG. 3 is a schematic view of an alternative embodiment of a patch according to the present invention.
Figure 4:
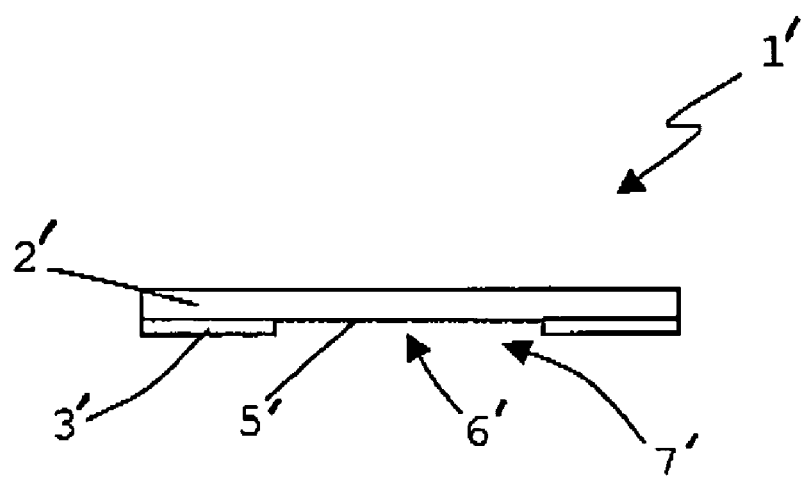
FIG. 4 is a cross-sectional view of the patch of FIG. 3.

Referring to FIGS. 3 and 4, an alternative embodiment of the patch of the present invention is described. Patch 1' includes electrostatic support 2 and adhesive 3' that is distributed on a peripheral portion of support 2'. Support 2' is circular and includes circular depression 7' formed in a center portion of support 2' by the absence of adhesive 3', as shown in FIG. 4'. Powdered allergen 5' is distributed over central non-adhesive surface 6' of support 2' and is coupled to non-adhesive surface 6' using electrostatic forces, as will be described in greater detail below. Preferably, support 2' has a diameter of approximately 12 mm and adhesive 3' is formed in a thin layer so that when patch 1' is applied, allergen 5' is substantially in contact with the skin. This circular embodiment may be especially useful for vaccination or for delivering small amounts of an allergen.

Figure 5:
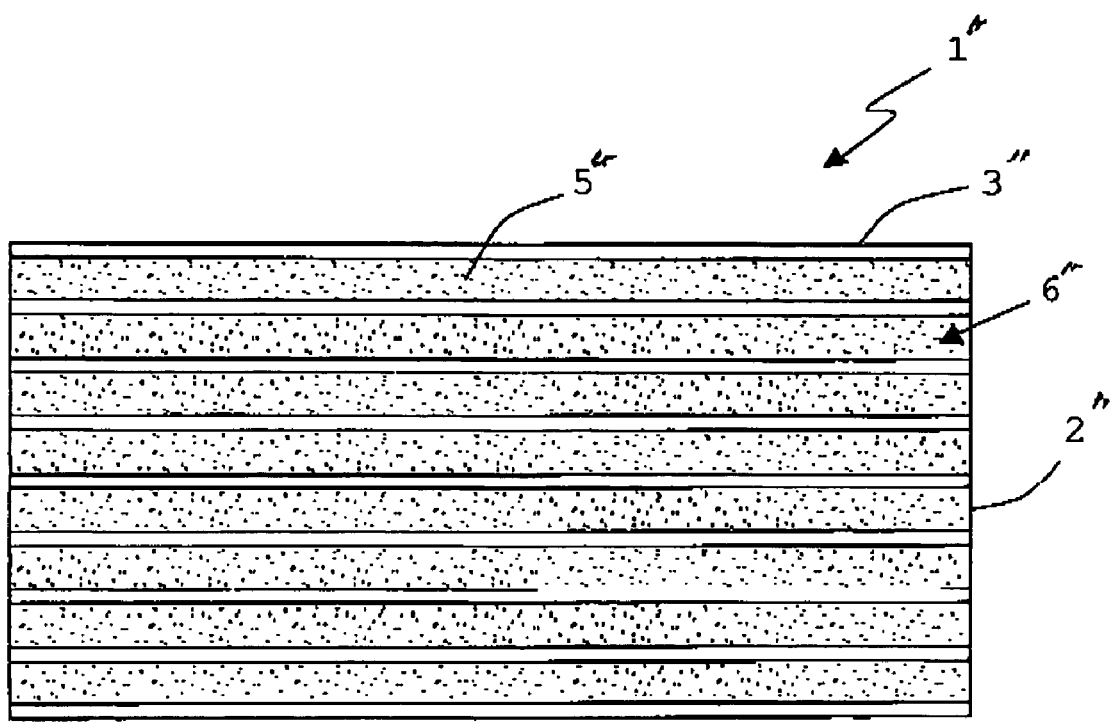
FIG. 5 is a schematic view of another alternative embodiment of a patch of the present invention.
Figure 6:
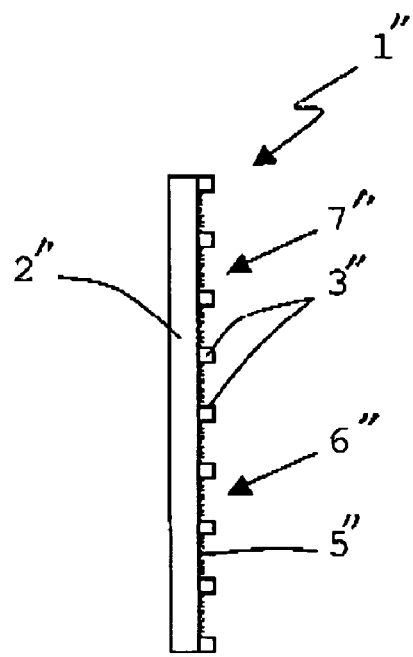
FIG. 6 is a cross-sectional view of the patch of FIG. 5.

Referring now to FIGS. 5 and 6, another alternative embodiment of the patch of the present invention is described. Similar to the previously described embodiments, patch 1" includes electrostatic support 2", adhesive 3" distributed over a portion of support 2" and allergen 5" distributed over strips of non-adhesive surface 6" of support 2". Support 2" illustratively is rectangular and adhesive 3" is distributed in parallel strips that extend longitudinally along support 2". Allergen 5" is distributed over the strips of non-adhesive surface 6" of support 2", interposed between the strips of adhesive 3". Preferably, the strips of adhesive 3" are more narrow than the strips of non-adhesive surface 6". Such a configuration may be particularly well-suited to deliver large amounts of allergen 5".

Figure 7:
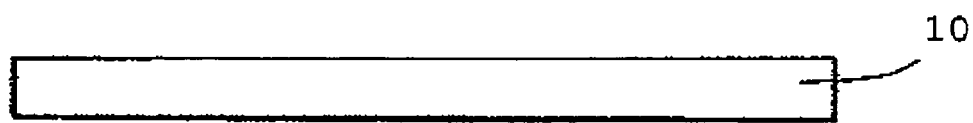
FIG. 7 is a side view of a film material used to create an electrostatic support according to the present invention.
Figure 8:
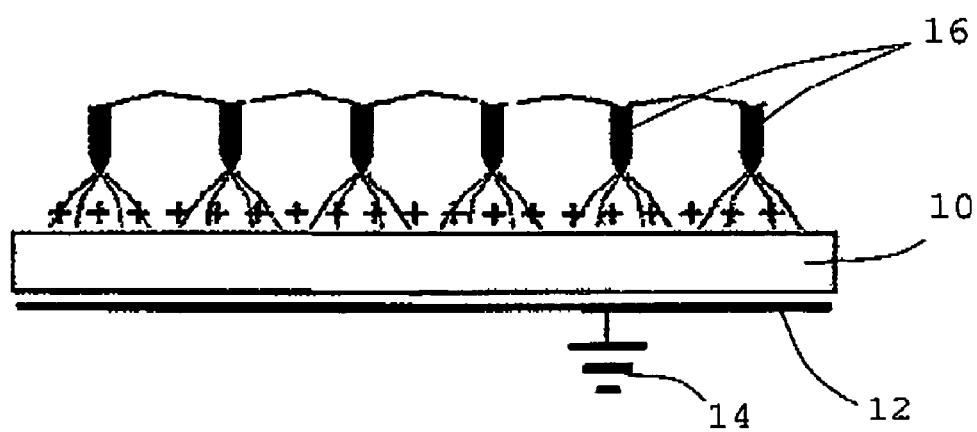
FIG. 8 is a schematic view illustrating a step of a process for creating an electrostatic support according to the present invention; the polarity of the arrows can also be positive.
Figure 9:
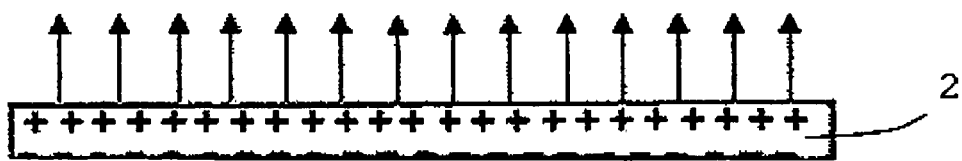
FIG. 9 is a side view of an electrostatic support according to the present invention; E with an arrow designates the electrostatic field. Alternatively, the support may comprise negative charges, the field being in the other orientation.

With respect to FIGS. 7-9, a method of enhancing, or creating, electrostatic forces on an electrostatic support, such as supports 2, 2' and 2", are described. First, polar or non-polar film 10, such as a 50 micrometer thick film of polyethylene, is selected. Film 10 is placed on plate 12 that is electrically coupled to electrical ground 14. Plate 12 is heated to approximately 80° C. and film 10 then is exposed to an electric field having a potential of approximately 10 kV by sharp electric needles 16 that are spaced approximately 10 mm from film 10, as depicted in FIG. 8. The temperature and voltage are applied for approximately 15 minutes and film 10 then is cooled, without removing the voltage, thereby transforming film 10 into an electrostatic support suitable for use in making the patch of the present invention.

The polarity of needles 16 is chosen based on the natural polarity of the desired active substance. For example, milk powder tends to have a positive charge and the polarity of needles 16 is chosen to negatively charge the surface of film 10 that will be exposed to the powder.

It should be appreciated that a grid may be interposed between needles 16 and plate 12 to control the residual intensity of the electric field on the surface of film 10. It should also be appreciated that the method may include a step of rapidly cooling film 10 after applying the electrical field and heat. Any suitable heating and cooling devices may be used, such as electric heaters and/or fluid-based heaters and cooling devices.

Figure 10:
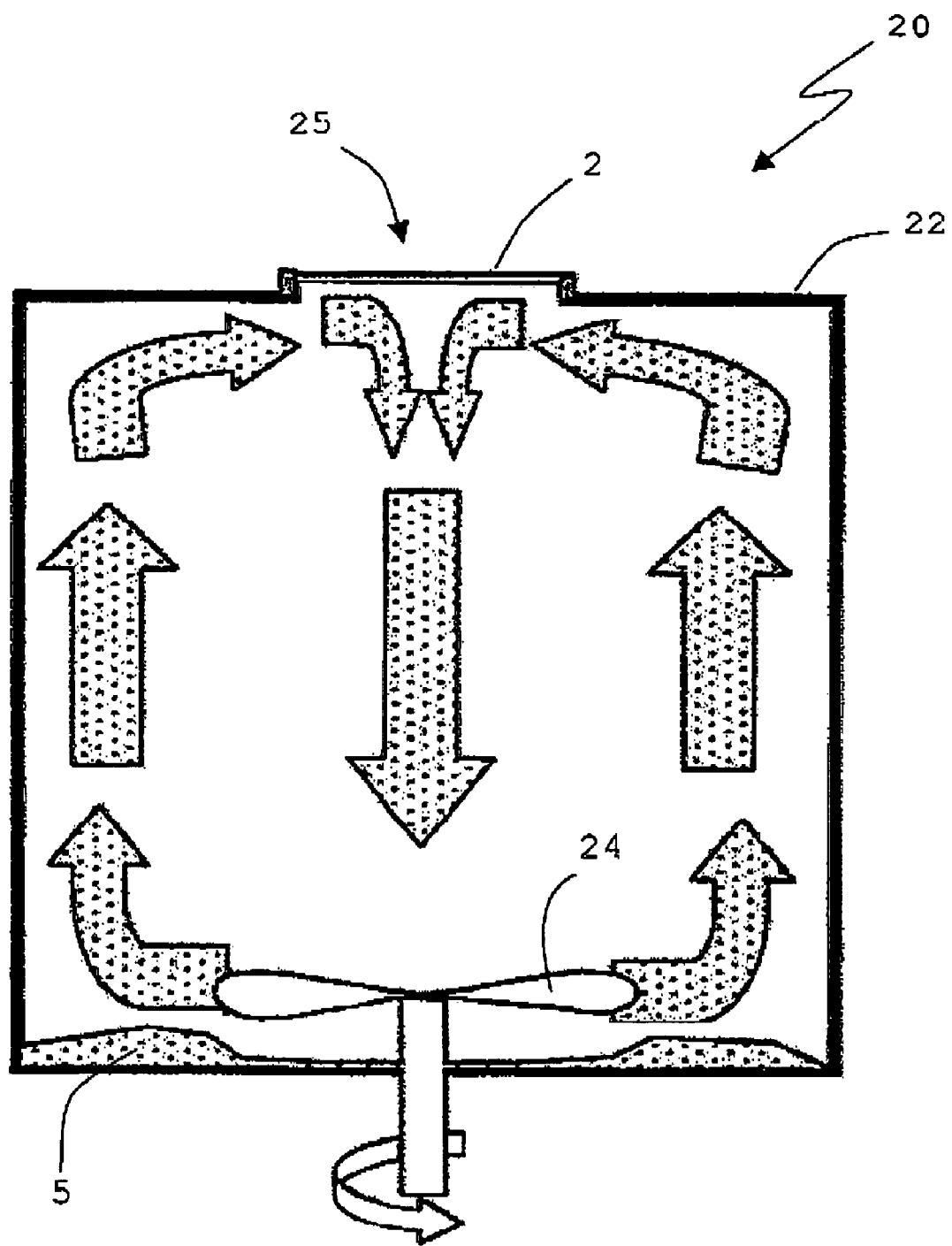
FIG. 10 is a cross-sectional view of a coating device by powder dipersion and collection on the patch.

Referring to FIG. 10, a preferred method of coating an electrostatic support, such as support 2, with powdered active substance, such as allergen 5, is described. Coating device 20 includes container 22 housing rotatable propeller 24. Container 22 defines a chamber for containing powdered allergen 5 during the coating process. Opening 25 is located at the top of container 22 and is circumscribed by centering flange 26, or other support device, which is configured to support and center an electrostatic support at opening 25, so that the surface of electrostatic support 2 to receive allergen 5 faces into container 22.

Propeller 24 is located at the bottom of container 22 and is configured to rotate within container 22. Propeller 24 may be rotated by any suitable means, such as an electric motor, so that its rotation causes air to circulate within container 22. Air circulating within container 22 causes powdered allergen 5, which is triboionized, to circulate within container 22 and contact electrostatic support 2. Allergen 5 adheres to electrostatic support 2 on contact, thus coating the electrostatic support with charged powder particles.

Alternative methods of coating electrostatic support 2 may be used. For example, powdered allergen 5 may be charged, for example, by using a corona effect. The charged powder then may be accumulated and electrostatic support 2 placed adjacent to the accumulated powder. Finally, an electrostatic field having a charge opposite to that of powdered allergen 5 may be created behind support 2 (i.e., so support 2 is interposed between the accumulated powder and the source of the electric field). The opposite charge of the electric field in comparison to the powder causes the powder to move towards the electric field and to impact support 2.

A further alternative method of coating support 2 may utilize industrial painting techniques. In particular, powdered allergen 5 is blown, with compressed air, past a needle having an electric potential of several thousand volts toward support 2. As powdered allergen 5 moves past the needle, it becomes charged by a corona effect and adheres to the oppositely charged support 2.

The quantity of powdered allergen 5 electrostatically held by support 2 depends on several factors, including the power of the electrostatic charge created on support 2. This in turn is a function of the distance between support 2 and allergen 5, and decreases rapidly as the distance between the two increases. As a result, more powerful charges on support 2 allow more active substance to be loaded thereon. In addition, the size and shape of the particles of powdered allergen 5 affects the quantity supported. As a result, it is preferred that the process for creating powdered allergen 5 be closely controlled for repeatability in the process for coating electrostatic support 2.

Example 1

Allergen Sensitivity

In this example, the effectiveness of the patches of the invention is compared with the effectiveness of patches of the prior art FINN CHAMBERS® type.

Means and Methods

A patch of the invention is applied to the back of 15 children. These children exhibit signs such that an allergy to cowls milk proteins (CMA) is suspected.

The patch has two areas; a first upper area consisting of an adhesive support onto which is deposited a tablet composed of powdered skimmed milk without any other associated element, which corresponds to the patch of the invention; the lower area consisting of the adhesive support onto which is deposited a cupule, the bottom of which is filled with diluted skimmed milk absorbed onto a cellulose pad of the FINN CHAMBERS® type.

Reading of the tests is carried out 48 hours later, after removal of the adhesive. The presence of erythematous or macular reaction indicates positivity.

Results

Fifteen (15) children aged five (5) weeks to eleven (11) years and three (3) months were tested for cow's milk allergy using a double patch. The reaction obtained was evaluated 48 hours after application of the patch.

All the children exhibited clinical signs suggesting a possible allergy to RGO cowls milk proteins, resistant to conventional therapeutic means (9 cases), eczema (6 cases), vomiting (2 cases), chronic abdominal pain (2 cases), chronic diarrhea (3 cases), unexplained manifestations of pain (4 cases), general feeling of being unwell (1 case).

The two tests were positive in three (3) cases and negative in ten (10) cases, the FINN CHAMBERS was positive and the patch negative in one (1) case and, conversely, the FINN CHAMBERS was negative and the patch positive in one (1) case.

Among these 15 children suspected of having a food allergy to cow's milk proteins, the patch of the present invention proved to be as sensitive as the FINN CHAMBERS method. In two cases, the results proved to be conflicting, without it being possible to distinguish the two methods.

Example 2

Epicutaneous Specific Immunotherapy

Figure 11:
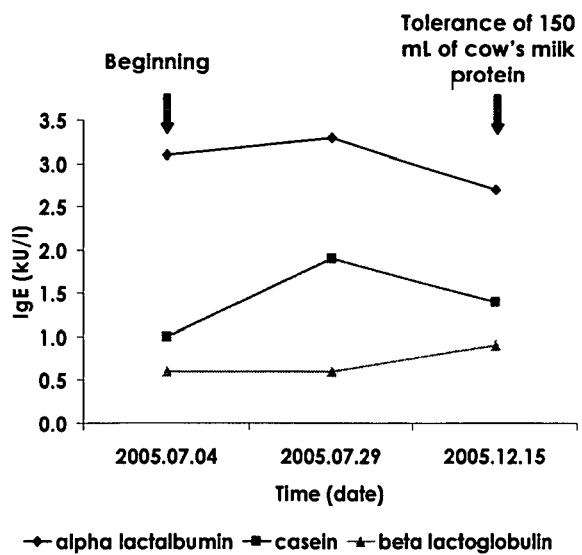
FIG. 11 shows that a patch of this invention can be used to desentitize a human subject to an allergen.
Figure 11:
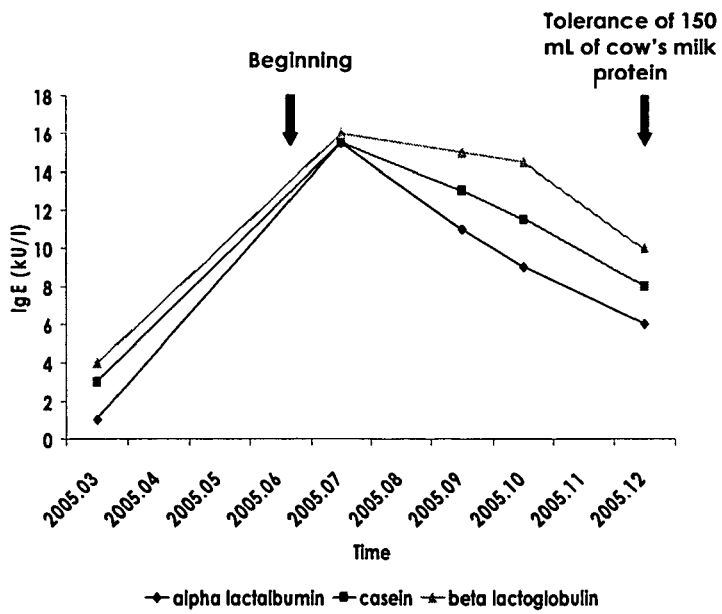

This example is to exemplify a method to desensitize food allergic individuals by applying therapeutic patches of this invention. A first attempt at desensitizing children via the epicutaneous route was carried out in 2 children with cow milk allergy manifested by immediate type reactions and elevated cow milk specific IgE. Epicutaneous patch tests containing 0,800 mg of milk powder were placed at the surface of the skin every three days and tolerance to milk quantified during standardized provocation procedures after one and two months, allowing determining precisely at which cumulated level of food the child reacts. As demonstrated in FIG. 11, both cases showed a progression of the amount of tolerated food, with at the end of the 1st month of treatment, an increase of cow milk specific IgE (important in one case and mild in the other one), which indicates that antigen-desensitization can be achieved using a patch of the present invention.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A patch, comprising:
   a support defining non-overlapping first and second regions, the support having an electrical charge impressed upon the first region by application of an electrical field to form an electrically charged surface;
   a predetermined amount of a powdered biologically active substance bound to the electrically charged surface in the first region through electrostatic forces; and
   an adhesive disposed only in the second region, the adhesive configured to seal the patch against a patient's skin form a moisture-retaining chamber.

2. The patch of claim 1, wherein the powdered biologically active substance has an electrical charge opposite to the electrical charge of the electrically charged surface of the support.

3. The patch of claim 1, wherein the second region subdivides the first region into a plurality of strips.

4. The patch of claim 1, wherein the first region comprises a plurality of linear, circular, or elliptic strips and the second region comprises a plurality of linear, circular, or elliptic strips interposed between adjacent strips of the first region.

5. The patch of claim 4, wherein the support is rectangular.

6. The patch of claim 1, wherein the first region is circular and the second region circumscribes the first region.

7. The patch of claim 6, wherein the second region is annular.

8. The patch of claim 7, wherein the support is disk-shaped.

9. The patch of claim 1, wherein the support is moisture impermeable.

10. The patch of claim 1, further comprising a label removably coupled to the adhesive.

11. The patch of claim 1, wherein the biologically active substance is selected from an allergen, an antigen and a biologically active polypeptide.

12. A method of manufacture of a skin patch, comprising:
    providing a support having a surface;
    applying an electrical field to the support to impress an electrical charge on the surface of the support to create an electrically charged surface;
    providing particles of a powdered active substance; and
    contacting the particles of the powdered active substance to the electrically charged surface so that the particles of the powdered active substance become bound to the electrically charged surface by electrostatic forces.

13. The method of claim 12, wherein impressing the electrical charge on the surface of the support comprises:
    selecting a support that can accumulate electrostatic charges;
    heating the support;
    applying an electric field to the support for a predetermined duration of time to electrically charge a surface of the support;
    cooling the film while continuing to apply the electric field to the support; and
    removing the electric field after the support is cooled.

14. The method of claim 13, wherein a polarity of the electric field applied to the support is selected to be opposite to a polarity of the powdered active substance.

15. The method of claim 12, wherein contacting the particles of the powdered active substance to the electrically charged surface comprises:
    circulating the powdered active substance within a container; and
    exposing at least a portion of the electrically charged surface to the circulating particles of the powdered active substance.

16. The method of claim 12, wherein contacting the particles of the powdered active substance to the electrically charged surface comprises blowing the particles of the powdered active substance toward the electrically charged surface with compressed air.

17. The method of claim 12, wherein contacting the particles of the powdered active substance to the electrically charged surface comprises attracting the particles of the powdered active substance toward the electrically charged using an electric field.

18. The method of claim 12, wherein providing the particles of the powdered active substance comprises:
    creating a solid form of an active substance by lyophilization or heating and spraying; and
    grinding the solid form to create solid particles having a predetermined and controlled size.

19. A method for testing the sensitization state of a subject with respect to an allergen, the method comprising applying the patch of claim 1 to the skin of the subject, wherein said biologically active substance is the allergen, and detecting the presence or absence of a skin reaction to the allergen.

20. A method for stimulating an immune response to an antigen in a subject, the method comprising applying the patch of claim 1 to the skin of the subject, wherein said biologically active substance is the antigen or an epitope thereof.

21. The method of claim 20, wherein the antigen is a polypeptide or a protein.

22. A method for delivering a drug to a subject, the method comprising a patch of claim 1 to the skin of the subject, wherein said biologically active substance is the drug.

23. The method of claim 22, wherein the drug is a polypeptide or a protein.

24. A patch, comprising:
a support having non-overlapping first and second portions, the first portion comprising a material capable of accumulating an electrostatic charge, the first portion having an electrically charged surface created by applying an electrical field to the first portion to impress an electrical charge thereon;
a layer of powdered active particles adhered to the first portion by contacting particles of a powdered active substance to the electrically charged surface; and
an adhesive disposed on the second portion, the adhesive configured to adhere the patch to skin.

25. The patch of claim 24, wherein the electrical charge is impressed onto the first region by heating the support, applying the electric field for a predetermined duration of time, cooling the support while continuing to apply the electric field, and then removing the electric field after the support has cooled.

26. The patch of claim 24, wherein the particles of powdered active substance have an electrical charge opposite to an electrical charge of the electrically charged surface.

27. The patch of claim 24, wherein contacting the particles of the powdered active substance to the electrically charged surface comprises:
circulating the particles of powdered active substance within a container; and
exposing at least a portion of the electrically charged surface to the circulating particles of the powdered active substance.

28. The patch of claim 24, wherein contacting the particles of the powdered active substance to the electrically charged surface comprises blowing the particles of the powdered active substance toward the electrically charged surface with compressed air.

29. The patch of claim 24, wherein contacting the particles of the powdered active substance to the electrically charged surface comprises attracting the particles of the powdered active substance toward the electrically charged using an electric field.

30. The patch of claim 24, wherein providing the particles of the powdered active substance comprises creating a solid form of an active substance by lyophilization or heating and spraying and then grinding the solid form to create solid particles having a predetermined and controlled size.

31. The patch of claim 24, wherein the second region subdivides the first region into a plurality of strips.

32. The patch of claim 31, wherein the first region comprises a plurality of linear, circular, or elliptic strips and the second region comprises a plurality of linear, circular, or elliptic strips interposed between adjacent strips of the first region.

33. The patch of claim 24, wherein the support is rectangular.

34. The patch of claim 24, wherein the first region is circular and the second region circumscribes the first region.

35. The patch of claim 34, wherein the second region is annular.

36. The patch of claim 24, wherein the support is moisture impermeable.

37. The patch of claim 24, further comprising a label removably coupled to the adhesive.

38. The patch of claim 24, wherein the powdered active substance is selected from an allergen, an antigen and a biologically active polypeptide.

39. The patch of claim 1 wherein the support comprises glass or a polymer.

40. The patch of claim 39, wherein the support is selected from amongst the group consisting of: glass, cellulose plastics, polyethylene, polyester, polyvinyl chlorides, polypropylenes, polystyrenes, polycarbonates, polyacrylics, and fluoropolymers.

41. The patch of claim 24 wherein the support comprises glass or a polymer.

42. The patch of claim 41, wherein the support is selected from amongst the group consisting of: glass, cellulose plastics, polyethylene, polyester, polyvinyl chlorides, polypropylenes, polystyrenes, polycarbonates, polyacrylics, and fluoropolymers.

* * * * *